(12) United States Patent
Bogen (10) Patent No.: US 9,486,726 B2
(45) Date of Patent: Nov. 8, 2016

(54) SEPARATION, SEDIMENTATION AND SEGREGATION CHAMBER WITH DUAL PORE-SIZE FILTER

(76) Inventor: Etai Bogen, Ramat-Hasharon (IL)

(*) Notice: Subject to any disclaimer, the term of this patent is extended or adjusted under 35 U.S.C. 154(b) by 0 days.

(21) Appl. No.: 13/261,703

(22) PCT Filed: Feb. 23, 2012

(86) PCT No.: PCT/IL2012/000090
§ 371 (c)(1),
(2), (4) Date: Aug. 1, 2013

(87) PCT Pub. No.: WO2012/114335
PCT Pub. Date: Aug. 30, 2012

(65) Prior Publication Data
US 2014/0154641 A1    Jun. 5, 2014

(30) Foreign Application Priority Data
Feb. 24, 2011    (IL) .......................................... 211397

(51) Int. Cl.
| | |
|---|---|
| *B01D 36/04* | (2006.01) |
| *A61C 17/02* | (2006.01) |
| *B01D 29/54* | (2006.01) |
| *A61C 17/06* | (2006.01) |
| *B01D 21/00* | (2006.01) |
| *B01D 29/58* | (2006.01) |
| *B01D 21/26* | (2006.01) |
| *B01D 35/157* | (2006.01) |
| *B01D 35/143* | (2006.01) |

(52) U.S. Cl.
CPC ......... *B01D 36/045* (2013.01); *A61C 17/0208* (2013.01); *A61C 17/046* (2013.01); *B01D 21/0012* (2013.01); *B01D 21/267* (2013.01); *B01D 29/54* (2013.01); *B01D 29/58* (2013.01); *B01D 35/1435* (2013.01); *B01D 35/1573* (2013.01); *B01D 2221/10* (2013.01)

(58) Field of Classification Search
CPC .. B01D 21/267; B01D 36/045; B01D 29/58; B01D 2221/10; B01D 35/1435; B01D 29/54; B01D 35/1573; A61C 1/0076; A61C 17/046; A61C 17/0208; F16K 15/18; F16K 15/183; F16K 15/186
USPC .............. 210/90, 304–306, 311, 315; 433/92
See application file for complete search history.

(56) References Cited

U.S. PATENT DOCUMENTS

| | | | | |
|---|---|---|---|---|
| 3,127,255 A | * | 3/1964 | Winslow ............ | B01D 21/0009 210/130 |
| 3,219,056 A | * | 11/1965 | Dyson .................. | F01D 17/145 137/514.7 |
| 4,298,465 A | * | 11/1981 | Druffel .............. | B01D 17/0211 210/304 |
| 5,044,953 A | * | 9/1991 | Sullivan .......................... | 433/92 |

(Continued)

*Primary Examiner* — Matthew O Savage (57) ABSTRACT

The present application discloses a method and apparatus for settling particles from waters that come out of plants that produce waste waters with hazardous components, utilizing vacuum power generated by vacuum generator down the waist water draining line. The method comprising a device with separation and sedimentation chamber, that allows phase separation through a unique cyclone-generating design, which leads to a filtering-chamber equipped with a dual pore-size filter that allows significant segregation of particles by particle size and mass, and thus allows highly efficient separation of hazardous particles from the waste water, which could exit the apparatus of present invention with significantly low content of hazardous particles.

11 Claims, 9 Drawing Sheets

(56) References Cited

U.S. PATENT DOCUMENTS

| | | | | |
|---|---|---|---|---|
| 5,478,484 A * | 12/1995 | Michaluk | | 210/788 |
| 5,885,076 A * | 3/1999 | Ralls et al. | | 433/92 |
| 6,331,246 B1 * | 12/2001 | Beckham | A61M 1/0056 | 137/545 |
| 6,471,853 B1 * | 10/2002 | Moscaritolo | B01D 35/143 | 210/143 |
| 6,761,822 B1 * | 7/2004 | Rhyne | B01D 27/06 | 210/253 |
| 2001/0047958 A1 * | 12/2001 | Estep | B01D 29/15 | 210/433.1 |
| 2004/0016691 A1 * | 1/2004 | Smit | A61M 1/0056 | 210/304 |
| 2010/0297577 A1 * | 11/2010 | Cohen | | 433/92 |
| 2012/0074069 A1 * | 3/2012 | Ripley | B01D 35/1435 | 210/741 |

* cited by examiner

SEPARATION, SEDIMENTATION AND SEGREGATION CHAMBER WITH DUAL PORE-SIZE FILTER

TECHNICAL FIELD

The invention relates to an apparatus for filtering waste waters laden with hazardous particles, which could range from toxic metals, biological hazardous materials, and any hazardous solid or semi-solid particles.

BACKGROUND ART

Industrial, medical, dental, scientific and environment rehabilitation plants can release waters laden with hazardous particles. Despite numerous attempts in the prior art, there is still a need for simple and cost effective, yet innovative device that could be installed in a flexible manner across the drainage lines that drain such a hazardous waters.

Medical facilities are the second largest waste producers, being second only to food industry. Dental clinics produce both biological and chemical waste that is related to surgical and restorative procedures respectively. Efforts to minimize the environmental hazards of dental waste have focused for decades mainly on mercury and other metals and toxic chemicals in typical dental waste. However, while the use of amalgam in restorative dentistry has declined sharply in recent decades we are witnessing a steep surge in invasive surgical procedures in dentistry that rather produce waste with blood and significantly hazardous biological components.

The dental field is an example of specialty area with an endless stream of emerging products to challenge with highly particle loaded water with hazardous properties. The infrastructure and manpower constraints present in a typical dental office requires that the equipment and apparatus used for the removal of wastes from dental effluent be of a reasonable operational and handling simplicity along with ultra-safe mounting and dismounting procedures. The apparatus should also not require substantial ongoing maintenance or downtime, and should be able to be operated in a self-sufficient manner for extended periods of time.

Any system for the removal and storage of hazardous waste products from dental effluent in a clinical setting should avoid the production of derivatives or byproducts that could be harmful upon exposure or release into the environment.

A number of devices have been described that are designed to remove waste products from dental effluents. These devices include one or more aspects such as gravity sedimentation of particles (e.g. U.S. Pat. Nos. 6,592,752, 5,885,076, 5,795,159, US 200100479561A1, U.S. Pat. Nos. 5,795,159 and 4,732,739), centrifuges designed to separate the heavier toxic metallic particles such as mercury from the effluent, ion-exchange systems for binding and removing charged molecules (e.g. U.S Pat. No. 5,885,076), and the use of chemical agents such as precipitants (e.g. 5,885,076, US 200100479561A1), chelating agents, flocculants, or adsorbants (e.g. U.S. Pat. Nos. 6,592,752, 6,592,754, US 200100479561A1). Acid-base adjustment, for example in mix tanks, has also been used in order to adjust the pH conditions to promote mercury precipitation in some systems (JP60197285A2, U.S. Pat. No. 6,592,752). Other sedimentation methods or pump filtration systems rely on mechanical filtration for the removal of mercury and other hazardous materials (e.g. U.S. Pat. Nos. 6,592,752, 5,885,076, 5,795,159, 6,592,754, 5,795,159. Such filters optionally incorporate methods based on ion-exchange, pH adjustment and absorbent columns (U.S. patent application Ser. No. 2001/0047956).

The entire prior art lacks the step of eliminating the biological component in such separators which is an essential step in tackling the bioconversion of mercury. Mercury is transformed into methylmercury when the oxidized or mercuric species (Hg2+), gains a methyl group (CH3). The methylation of Hg2+ is primarily a biological process resulting in the production of highly toxic and bioaccumulative methylmercury compounds (MeHg+). Although the exact mechanism by which bacteria biomethylizes inorganic Mercury into the organic methylmercury is not known precisely, the consequences of this bioconversion is well known. Methylmercury compounds that are produced by this bioconversion are more soluble derivatives of mercury and subsequently are more able to build up in living tissue and increase in concentration up the food chain, up to humans, once released to the waste collecting and processing system. Methylmercury compounds are responsible for birth defects and nervous disorders in people exposed to methyl mercury through their food.

Thus, microorganism proliferation in bottom sediment and sludge in dental office waste separators could play a hazardous role in mercury bioconversion if a recycling process of dental waste does not include a step of eliminating the biological component in a dental waste separator, before removing the residing insoluble or soluble mercury from the separator.

Hence, an innovative and eco-friendly system and apparatus is provided herewith for managing the biological waste component, beside metallic and chemical components of the dental waste.

DISCLOSURE OF INVENTION

The present invention provides a method and apparatus for settling particles from waters that comes out of plants that produce waste waters with hazardous components, utilizing vacuum power generated by vacuum generator down the waste water draining line. The method comprising a device with separation and sedimentation chamber, that allows phase separation through a unique cyclone-generating design, which leads to a filtering-chamber equipped with a dual pore-size filter that allows significant segregation of particles by particle size and mass, and thus allows highly efficient separation of hazardous particles from the waste water, which could exit the apparatus of present invention with significantly low content of hazardous particles. Other aspects and advantages of the invention will be apparent from the following description and the appended claims.

BEST MODE FOR CARRYING OUT THE INVENTION

The present Invention discloses a method and apparatus for settling particles from waters that come out of plants that produce waste waters with hazardous components, utilizing vacuum power generated by vacuum generator down the waist water draining line.

It should be noted that identical features in different drawings are shown with the same reference numeral.

Figure 1:
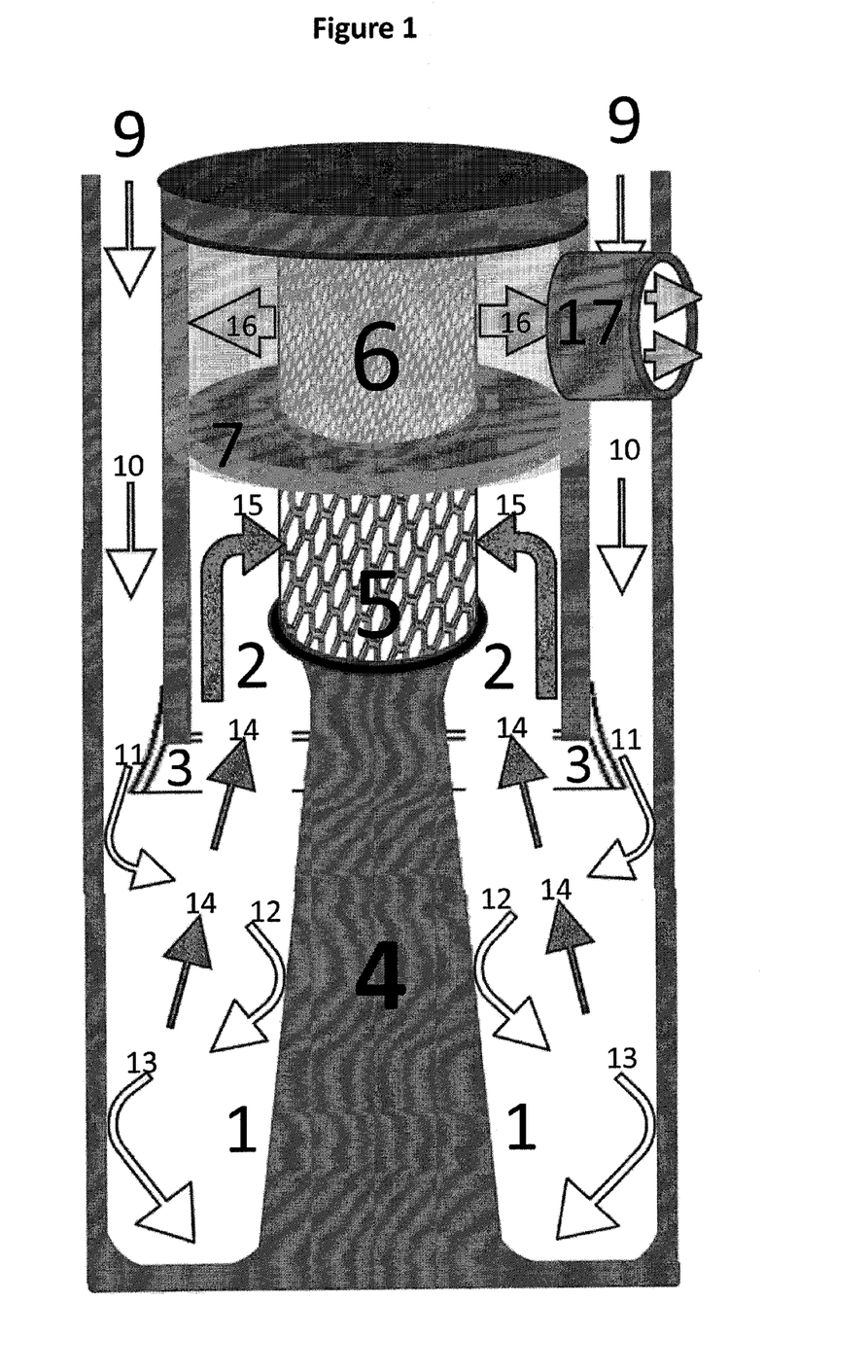
FIG. 1 shows a diagram of main parts of apparatus of current invention, showing the separation and sedimentation chamber and the filtration chamber with the dual pore-size filter in a higher-pore-size-first assembly.
Figure 2:
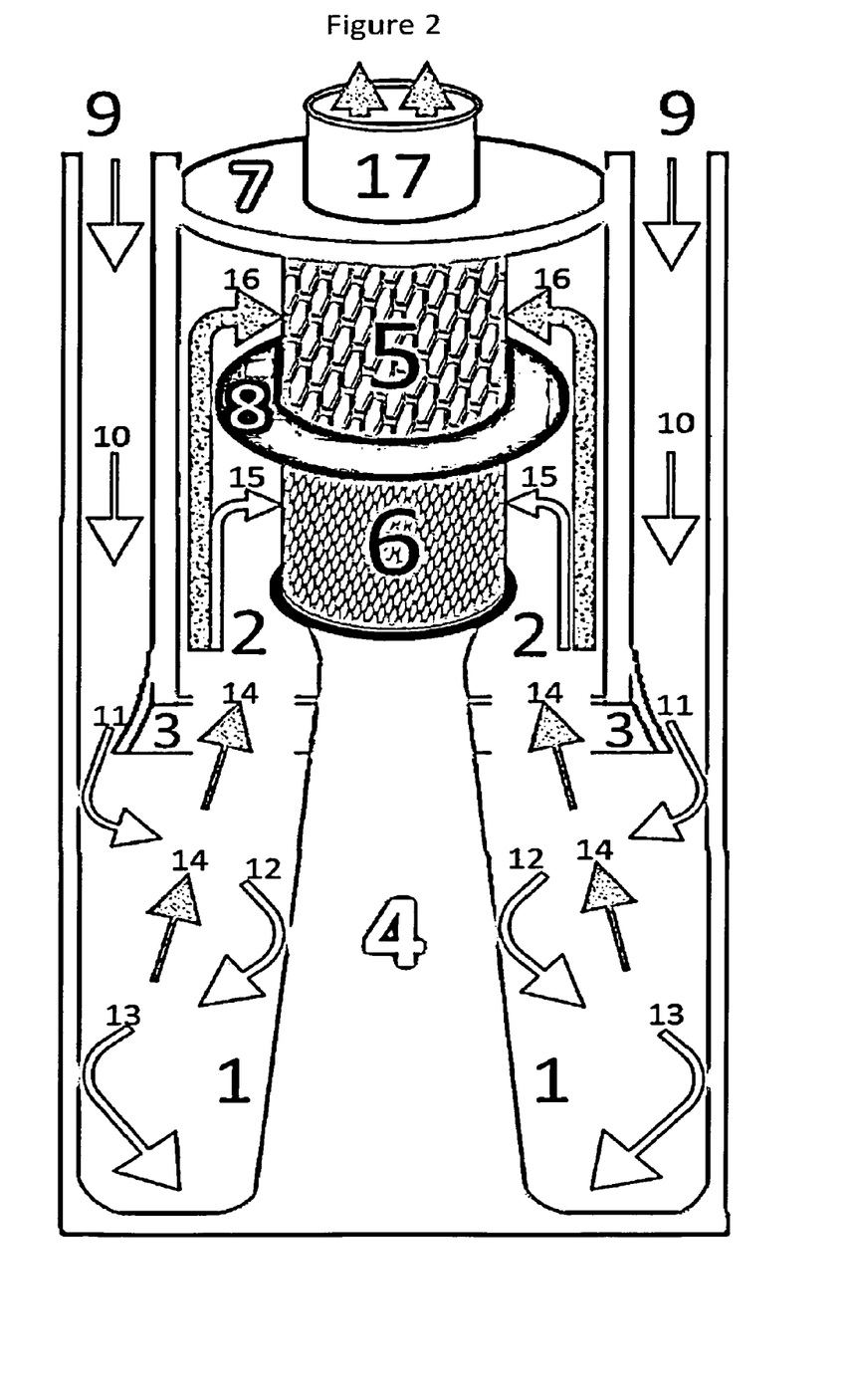
FIG. 2 shows a diagram of main parts of apparatus of current invention, showing the separation and sedimentation chamber and the filtration chamber with the dual pore-size filter in a lower-pore-size-first assembly.

FIGS. 1 and 2 show cross-sectional view of main parts of the invented apparatus.

The movement of the waste water across the apparatus is powered by a vacuum generator at the far end of the drainage line. Waste water enters at the top 9 of the device. While flowing downward, the water stream hits a winged edge 3 designed to initiate a cyclonic movement 11 that will drive the water jet toward the outer wall, and then to hit the medial conical structure 4, and to rebound back 12 toward the outer wall 13, in a repeated cycles that will end eventually by hitting the ground of the separation chamber 1. After hitting the ground of the chamber, an ascending jet of water 14 will head through the inner aspect of wing 3 to the filtration chamber 2, derived by the vacuum force. In accordance with one embodiment of the present invention (FIG. 1), the ascending jet 15 will hit first the deflection wing 7 that separates the two half-filters. The way out of jet 15 will be first through the higher-pore-size filter 5 thus causing paticles larger than this particular pore-size to stay out of the filter lumen. The jet then ascends in the lumen and hit the lower-pore-size filter 6 from its inner aspect, thus preventing smaller particles with size larger than the pore-size of upper filter 6 from exiting the device with water jet 16 toward the exit 17. In an alternative embodiment (FIG. 2), ascending jet of water 14 will face, upon entering the filtration chamber 2, a smaller-pore-size first arrangement, with the two half-filters separated by deflection wing 8 that will cause the particles in the jet to separate further by particle size. The lower sized particles 15 will be segregated by the lower-pore-size filter 6 and the remaining jet will ascend directly to the exit 17, while the larger sized particles will proceed with the jet 16 and will be segregated by the higher-pore-size filter 5 with the remaining jet entering the lumen toward exit 17.

Figure 3:
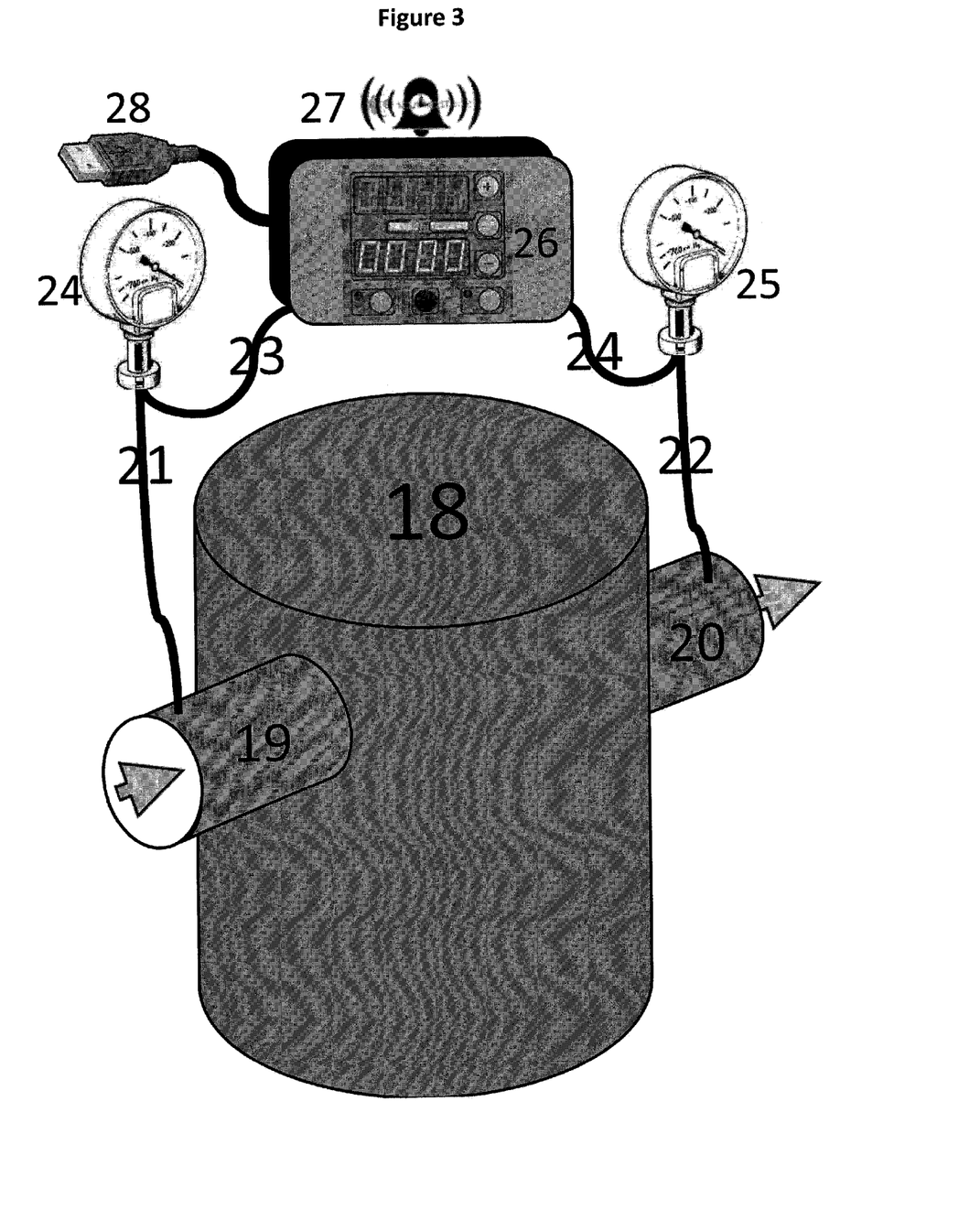
FIG. 3 shows the connection of the apparatus of current invention to a control unit that controls the vacuum gradient between the inlet and outlet sides of the device.

FIG. 3 shows the apparatus of current invention 18 with both inlet 19 and exit 20 connected to vacuum gauges 24 and 25 (by tubes 21 and 25) and to control unit 26 (by tubes 23 and 24). The control unit 26 will control the vacuum gradient between the inlet and outlet sides of the device, and thus could calculate, according to pre-determined thresholds, when to report the need to replace the used 'settling and filtering unit' with new one, through a connection to a computer 28 or by triggering an audio-visual alarm 27.

Figure 4:
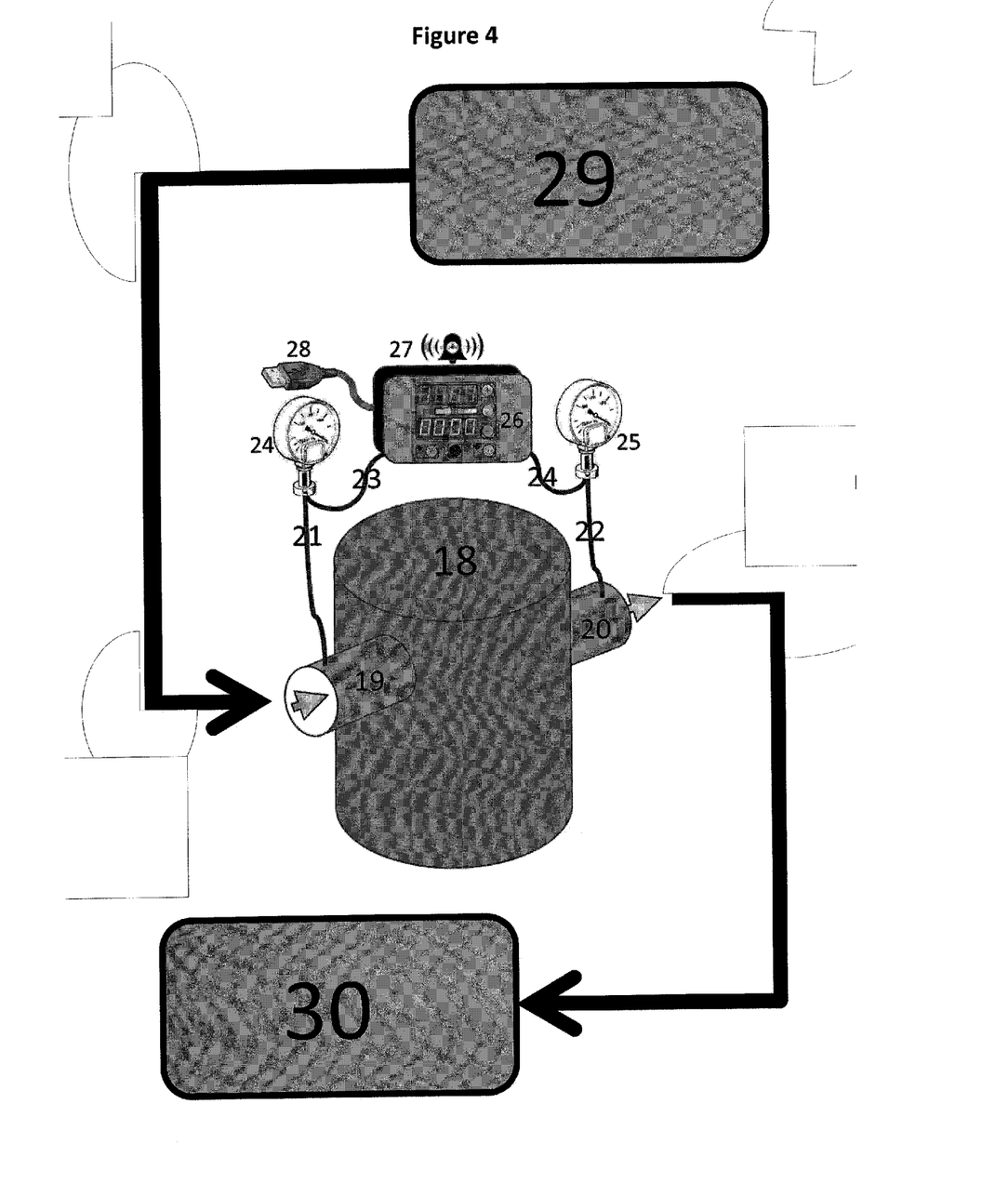
FIG. 4 shows that the apparatus of current invention could be installed at any stage of the vacuum powered line, between the drainage from the waste generating plant and the vacuum powered waste collecting point.

FIG. 4 shows that the apparatus of current invention 18 could be installed at any position across the vacuum powered line, between the exit from the waste generating plant 29 and up to the inlet of the vacuum powered waste collecting point 30.

Figure 5:
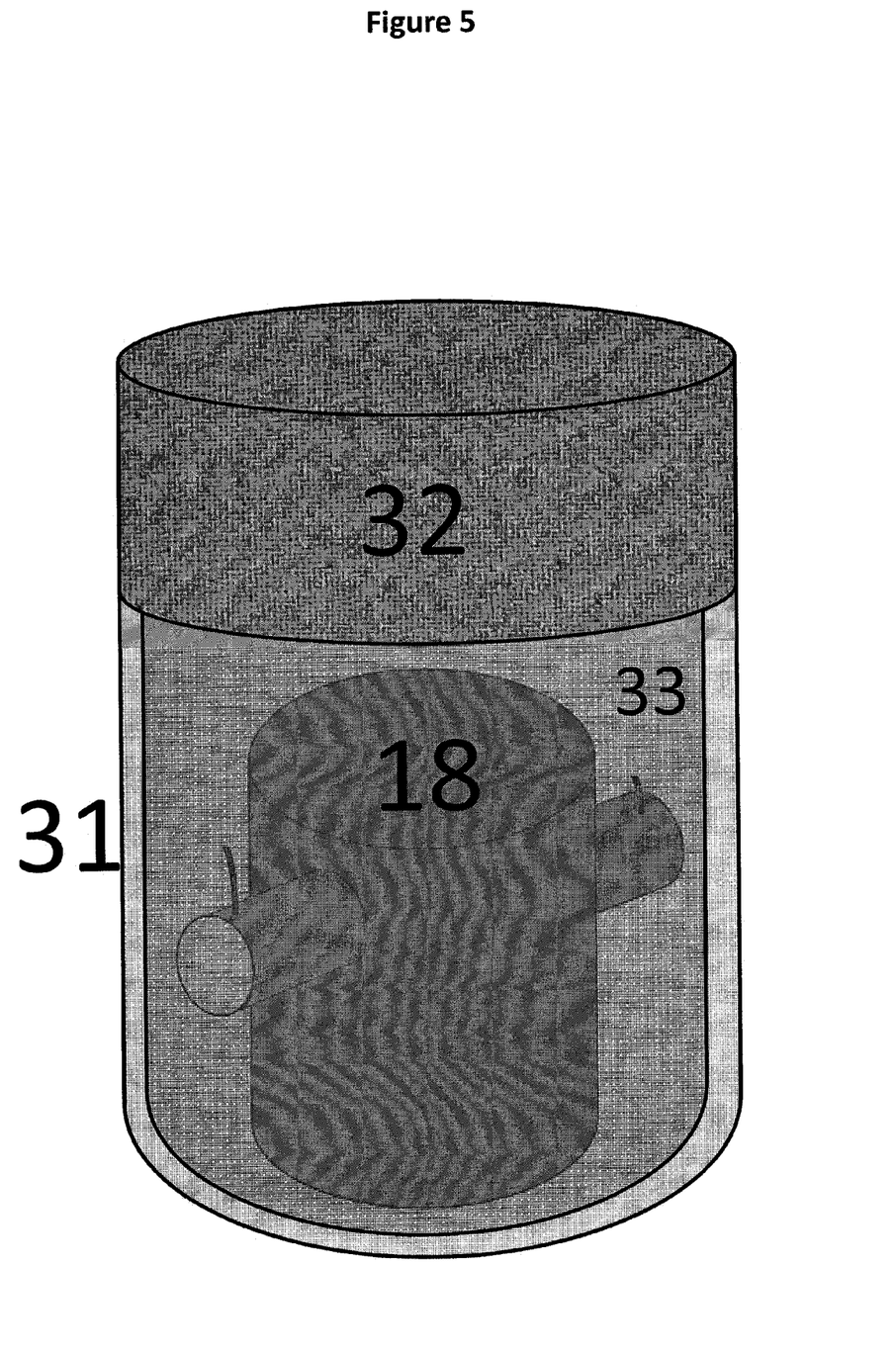
FIG. 5 shows that the apparatus of current invention could be safely dismantled from the waste vacuum line at the end of use, and safely enclosed in a tailored container with a tight seal.

At due time, the used unit 18 with the hazardous load could be easily dismantled (FIG. 5) and enclosed in a tailored container 31 with a tight seal 32, for a safe collection for detoxification and recycling purposes, with the possible addition of a detoxification or hazard neutralization materials 33 inside container 31.

Figure 6:
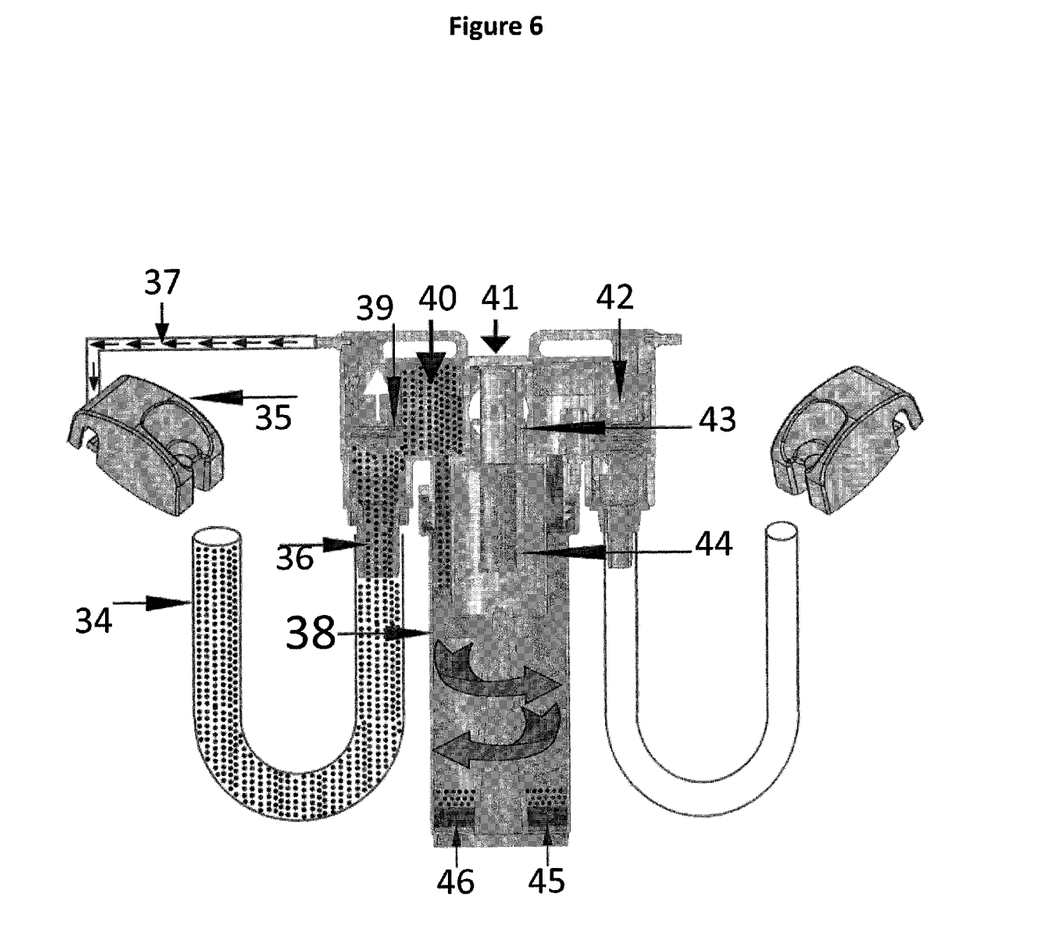
FIG. 6 shows an embodiment of current invention for use in processing waste generated by dental surgery unit.

FIG. 6 shows an embodiment of current invention for use in processing waste generated by dental surgery unit, showing suction tube 34 connected to the apparatus of current invention 38 at the orifice 36, while dental surgery unit holder 35 is connected by tube 37 to a valve 39 (or 42) that allows to enter the separation chamber through inlet 40, to settle in the bottom of the chamber 45 and 46, or to ascend and hit the dual pore-size filter 43 and 44, in a manner that was described in FIG. 1, before exiting at exit 41.

Figure 7:
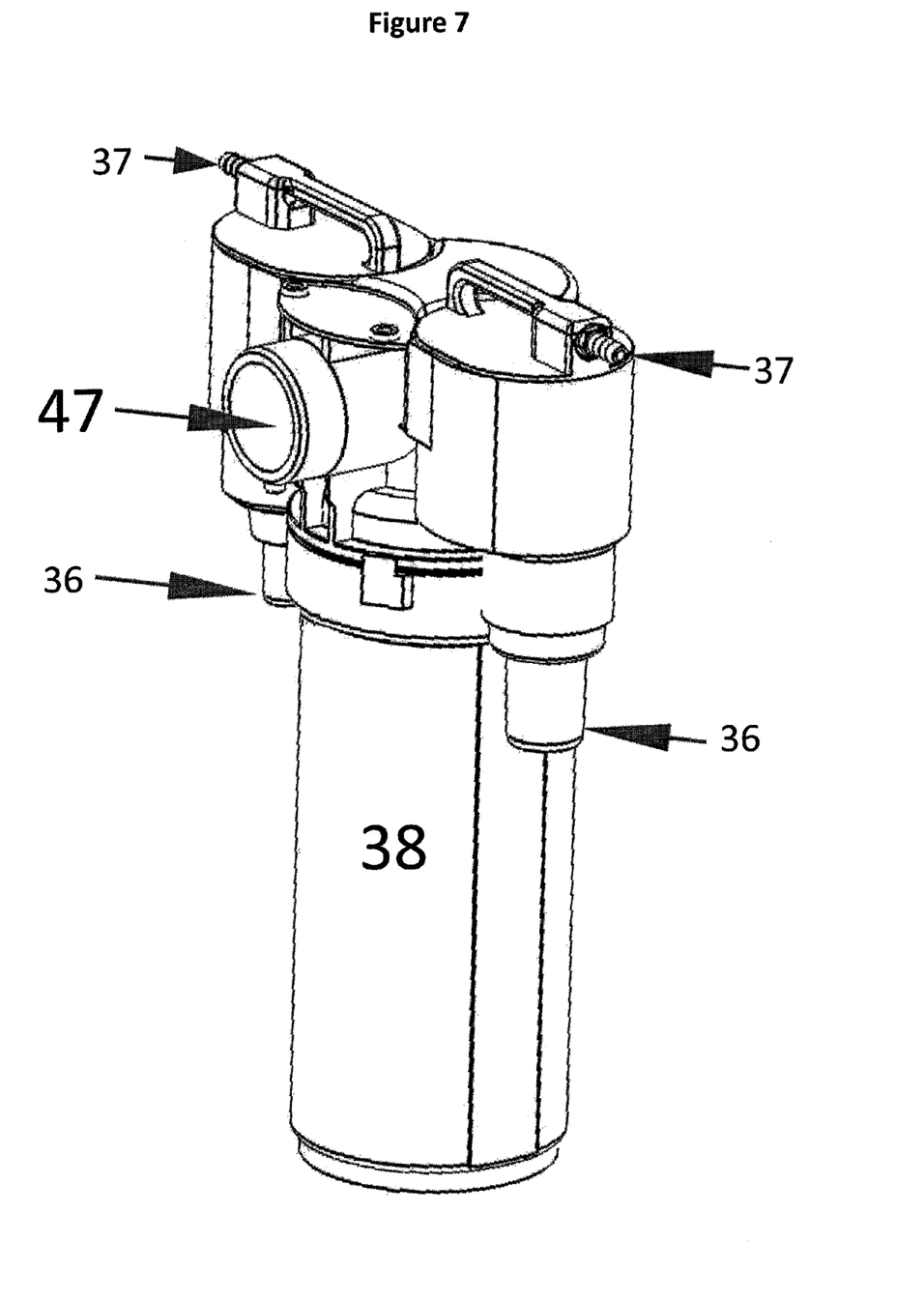
FIG. 7 shows an overview of the device for use in a dental surgery unit.

FIG. 7 shows an over view of the device 38 with inlet 36 and exit 47, and ports for control of inlet valves 37.

Figure 8:
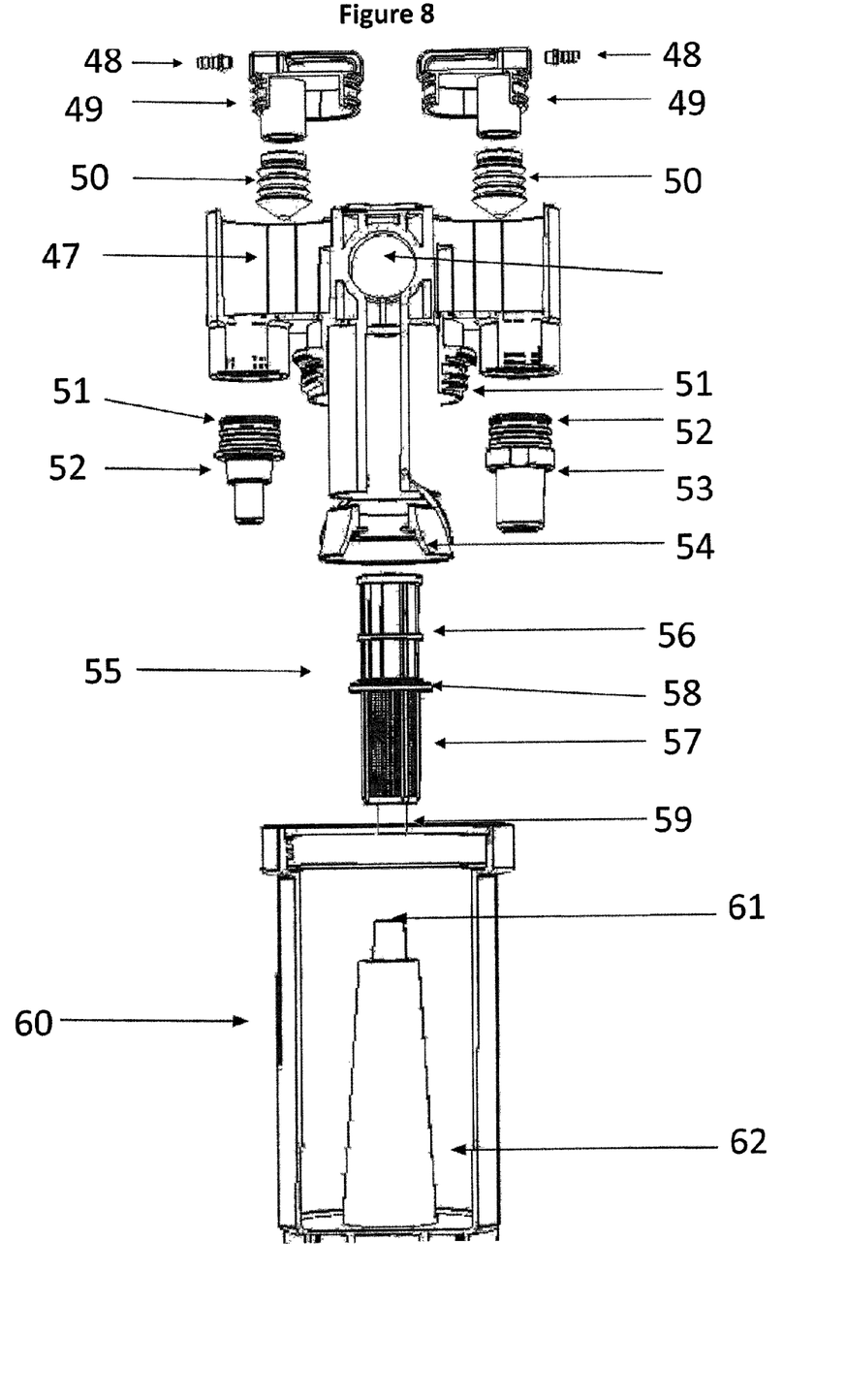
FIG. 8 shows a detailed description of the device for use in a dental surgery unit.

FIG. 8 shows detailed description of the device, showing controllers 48 of inlet valves 49 and 50. Further, the upper part of the device is shown with exit orifice 47, screw joint 51, inlet fittings 52 and 53, and cyclone-generating wing 54. The dual filter 55 is shown with its two segments 56 and 57, separated by joint and sealing o-ring 58, and the base axis 59 for assembly on joint 61 of lower chamber 62 body 60.

Figure 9:
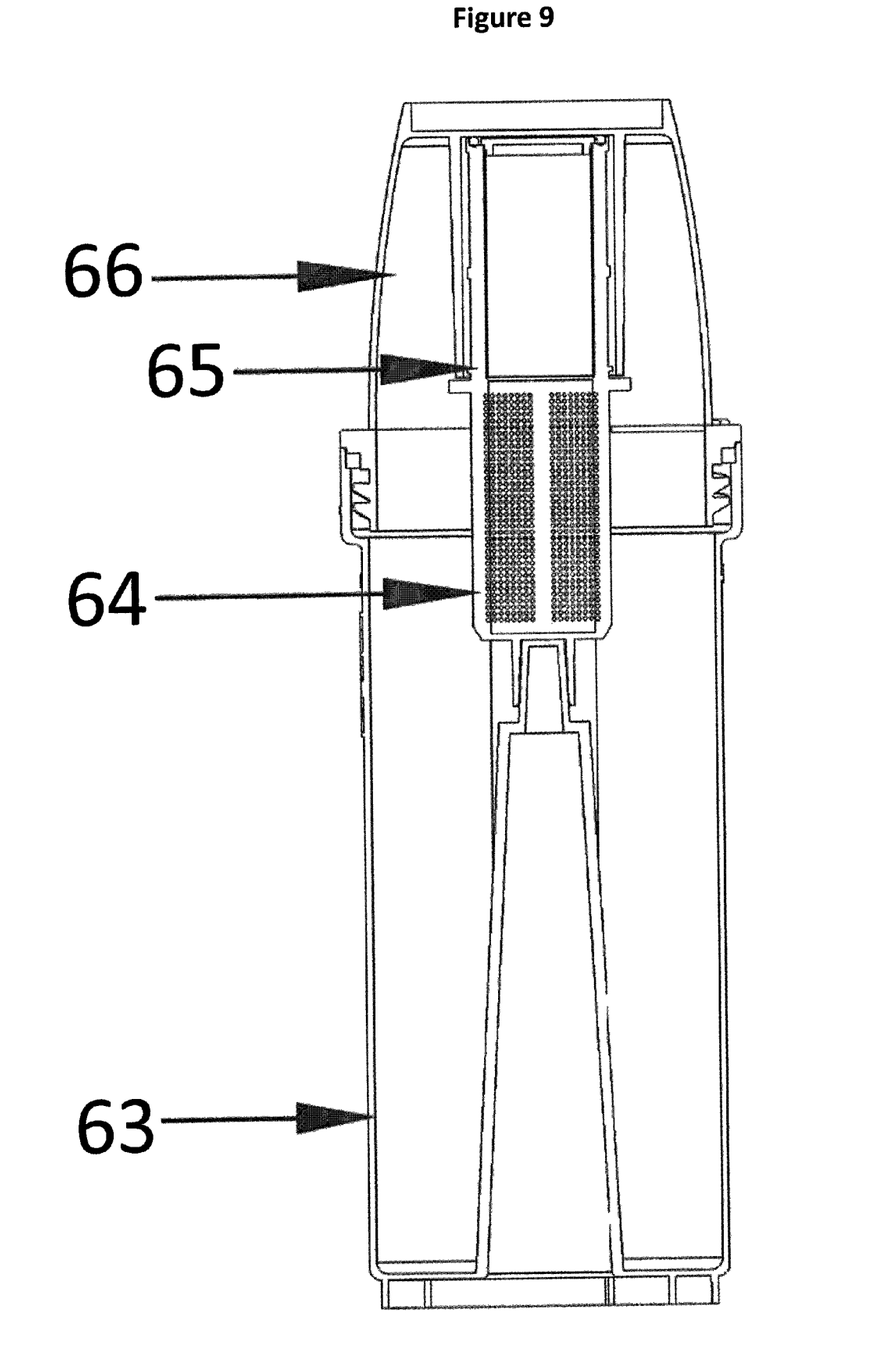
FIG. 9 shows that the device for dental use could be removed safely and enclosed in a tightly closed container.

FIG. 9 shows that the device for dental use 63 could be removed safely with the filters 64 and 65 and simply closed with a tightly closed cover 66.

In summary, a device for settling particles from waters that comes out of plants that produce waste waters with hazardous components has been disclosed. The device includes a housing 60 having a cylindrical sidewall, an open top, a closed bottom wall, and a medial conical structure 62 extending upwardly from the closed bottom wall, wherein a bottom end of the medial conical structure has a larger diameter than upper portions of the medial conical structure (see FIG. 8). A filter head is provided for closing the upper open end of the cylindrical housing, wherein the filter head includes a cylindrical wall that extends coaxially within the cylindrical sidewall of the housing, wherein an interior space within the cylindrical sidewall of the filter head defines a filtration chamber 2 (see FIG. 1), the filter head including two inlet passages symmetrically arranged on opposite sides of the cover and extending from an exterior of the filter head to a first annular space 10 located between the cylindrical sidewall of the housing and the cylindrical wall of the filter head (see FIGS. 1-2), the filter head including an exit passage 17/47 extending from an exterior of the cover to an upper portion of the filtration chamber (see FIGS. 1, 2, and 8), the cylindrical wall of the filter head having a bottom portion 3 that flares radially outwardly toward an inner surface of the cylindrical sidewall of the housing (see FIGS. 1-2), wherein the flared bottom portion includes at least one wing that extends in a spiral manner around an outer surface of the flared bottom portion for generating cyclonic movement in water flowing downwardly through the first annular space from the inlet passages (see FIG. 9), wherein a separation chamber 1 is defined below the bottom end of the cylindrical wall of the filter head and bounded by the cylindrical sidewall of the housing, the bottom wall of the housing, and an outer surface of the medial conical structure (see FIGS. 1-2). The device includes cylindrical filter element 55 having an upper section and a lower section surrounding a hollow interior (see FIG. 8). The filter element is located within the filtration chamber such that a second annular space is provided between an inner surface of the cylindrical wall of the filter head and an outer surface of the filter element (see FIGS. 1-2), wherein the upper section 56 is positioned adjacent the exit passage 17 and the lower section 57 has a bottom end that is closed and that is supported by an upper end 61 of the medial conical structure 62 (see FIG. 8), and wherein the upper section has a pore size that is different from a pore size of the lower section. As shown in FIG. 1, the upper section 6 has an upper end that is closed and an outer surface that is positioned adjacent to the exit passage 17, wherein a seal 7 is provided to separate an upper portion of the second annular space adjacent the upper section 6 from a lower portion of the second annular space adjacent the lower section 5, whereby water is filtered by flowing radially inwardly through the lower section and radially outwardly through the upper section to the exit passage. In FIG. 1, the upper section 6 of the cylindrical filter element can have a pore size in a range of 1-100 microns and the lower section 5 can have a pore size ranging from 50 to 1000 microns. In FIG. 1, the upper section 6 of the cylindrical filter element can also have a pore size in a range of 1 to 10microns and the lower section can also have a pore size in a range of 5-500 microns. In FIG. 2, the cylindrical filter element includes an annular deflection wing 8 extending around an outer periphery thereof between the upper section 5 and the lower section 6, whereby water is filtered by flowing radially inwardly through the upper section and the lower section. In FIG. 2, the upper section 5 of the cylindrical filter element can have a pore size in a range of 50 to 1000 microns and the lower section 6 can have a pore size ranging from 1-100 microns. In FIG. 2, the upper section 5 of the cylindrical filter element can also have a pore size in a range of 5-500 microns and the lower section can also have a pore size in a range of 1 to 10 microns. As shown in FIG. 8, each of the inlet passages can include a valve 50 for controlling flow through the respective inlet passage. As shown in FIG. 9, the device can include a cover for attachment to the upper open end of the housing, wherein the housing and the filter element can be removed from the filter head and the cover can be attached to the upper open end of the housing to seal the filter element within the housing.

INDUSTRIAL APPLICABILITY

The device of current invention could be manufactured from plastic materials, metals, rubber, or a combination of materials. The device could be manufactured at different scales, from a miniature device of little cubic millimeter capacity, which could be used to recover certain particles of interest, up to a large scale industrial device for handling high volumes of particle laden waters. In same manner, the pore sized of both low and high pore-sized filters could be tailored to a specific mission, with the smaller-pore-sized filter starting from the single micron scale and up, while the larger-pore-sized filter could start from few microns of pore size and up through ten or few tens of microns, and even higher, again according to the specific mission to which the device is designed for.

In general, the device could be used for settling particles from waters that come out of plants that produce waste waters with hazardous components, utilizing vacuum power generated by vacuum generator down the waist water draining line. Such plants could be part of industrial process, medical process, dental process, scientific process, or environment protecting process.

The invention claimed is:

1. A device for settling particles from waters that comes out of plants that produce waste waters with hazardous components, comprising:
   a housing having a cylindrical sidewall, an open top, a closed bottom wall, and a medial conical structure extending upwardly from the closed bottom wall, wherein a bottom end of the medial conical structure has a larger diameter than upper portions of the medial conical structure;
   a filter head for closing the upper open end of the cylindrical housing, wherein the filter head includes a cylindrical wall that extends coaxially within the cylindrical sidewall of the housing, wherein an interior space within the cylindrical sidewall of the filter head defines a filtration chamber, the filter head including two inlet passages symmetrically arranged on opposite sides of the cover and extending from an exterior of the filter head to a first annular space located between the cylindrical sidewall of the housing and the cylindrical wall of the filter head, the filter head including an exit passage extending from an exterior of the cover to an upper portion of the filtration chamber, the cylindrical wall of the filter head having a bottom portion that flares radially outwardly toward an inner surface of the cylindrical sidewall of the housing, wherein the flared bottom portion includes at least one wing that extends in a spiral manner around an outer surface of the flared bottom portion for generating cyclonic movement in water flowing downwardly through the first annular space from the inlet passages, wherein a separation chamber is defined below the bottom end of the cylindrical wall of the filter head and bounded by the cylindrical sidewall of the housing, the bottom wall of the housing, and an outer surface of the medial conical structure; and
   a cylindrical filter element having an upper section and a lower section surrounding a hollow interior, wherein the filter element is located within the filtration chamber such that a second annular space is provided between an inner surface of the cylindrical wall of the filter head and an outer surface of the filter element, wherein the upper section is positioned adjacent the exit passage and the lower section has a bottom end that is closed and that is supported by an upper end of the medial conical structure, and wherein the upper section has a pore size that is different from a pore size of the lower section.

2. The device according to claim 1, wherein the upper section has an upper end that is closed and an outer surface that is positioned adjacent to said exit passage, wherein a seal is provided to separate an upper portion of the second annular space adjacent the upper section from a lower portion of the second annular space adjacent the lower section, whereby water is filtered by flowing radially inwardly through the lower section and radially outwardly through the upper section to the exit passage.

3. The device of claim 2, wherein the upper section of the cylindrical filter element has a pore size in a range of 1-100 microns and the lower section has a pore size ranging from 50 to 1000 microns.

4. The device of claim 3, wherein the upper section of the cylindrical filter element has a pore size in a range of 1 to 10 microns and the lower section has a pore size in a range of 5-500 microns.

5. The device according to claim 1, wherein the cylindrical filter element includes an annular deflection wing extending around an outer periphery thereof between the upper section and the lower section, whereby water is filtered by flowing radially inwardly through the upper section and the lower section.

6. The device of claim 5, wherein the upper section of the cylindrical filter element has a pore size in a range of 50 to 1000 microns and the lower section has a pore size ranging from 1-100 microns.

7. The device of claim 6, wherein the upper section of the cylindrical filter element has a pore size in a range of 5-500 microns and the lower section has a pore size in a range of 1 to 10 microns.

8. The device according to claim 1, wherein each of the inlet passages includes a valve for controlling flow through the respective inlet passage.

9. The device according to claim 1, further comprising a control unit that monitors the vacuum gradient between the inlet passages and exit passage of the device, wherein the control unit is adapted to report the need to replace a used filter element with a new filter element by connection to computer or by triggering an audio and/or visual alarm.

10. The device according to claim 1, further comprising a container for containing the device and a neutralizing material, whereby the device and a neutralizing material can be tightly sealed within the container.

11. The device according to claim 1, further comprising a cover for attachment to the upper open end of the housing, wherein the housing and the filter element can be removed from the filter head and the cover can be attached to the upper open end of the housing to seal the filter element within the housing.

* * * * *